(12) United States Patent
Zhang et al.

(10) Patent No.: US 9,841,376 B2
(45) Date of Patent: Dec. 12, 2017

(54) HIGH SENSITIVITY METAMATERIAL NANO-SENSING SYSTEM WITH ULTRA-NARROW LINE WIDTH SPECTRAL RESPONSE

(71) Applicant: Xi'an Institute of Optics and Precision Mechanics of CAS, Xi'an (CN)

(72) Inventors: Wenfu Zhang, Xi'an (CN); Guoxi Wang, Xi'an (CN); Lingxuan Zhang, Xi'an (CN); Wei Zhao, Xi'an (CN)

(73) Assignee: XI'AN INSTITUTE OF OPTICS AND PRECISION MECHANICS OF CAS, Xi'an, Shaanxi (CN)

( * ) Notice: Subject to any disclaimer, the term of this patent is extended or adjusted under 35 U.S.C. 154(b) by 0 days.

(21) Appl. No.: 15/071,988

(22) Filed: Mar. 16, 2016

(65) Prior Publication Data

US 2017/0254751 A1    Sep. 7, 2017

(30) Foreign Application Priority Data

Mar. 1, 2016    (CN) .......................... 2016 1 01163325

(51) Int. Cl.
*G01N 21/55*    (2014.01)
*G01N 21/552*    (2014.01)
(52) U.S. Cl.
CPC ..... *G01N 21/554* (2013.01); *G01N 2201/061* (2013.01); *G01N 2201/068* (2013.01)

(58) Field of Classification Search
CPC .......... G01N 21/554; G01N 2201/061; G01N 2201/068
USPC ................................... 356/445–448
See application file for complete search history.

(56) References Cited

U.S. PATENT DOCUMENTS 8,865,078 B2 * 10/2014 Chiou .................... B82Y 15/00
                                                  356/73.1
2013/0130939 A1 * 5/2013 Wawro ................. G01N 21/253
                                                  506/18

* cited by examiner

*Primary Examiner* — Tri T Ton
(74) *Attorney, Agent, or Firm* — Pearl Cohen Zedek Latzer Baratz LLP

(57) ABSTRACT

The invention relates to a metamaterial nano-sensing system, and in particular to a high-sensitivity metamaterial nano-sensing system with an ultra-narrow line width spectral response. The system includes an input light path, a metamaterial nano-sensing unit and an output light path which are sequentially provided along a direction of a light path, and the metamaterial nano-sensing unit includes a Bragg grating and a metallic periodic array arranged above the Bragg grating. The nano-sensing system provided by the invention has an ultra-narrow line width spectral response, so that sensitivity of a nanosensor is effectively improved, and broad application prospect in the fields of portable biosensing, drug development and detection, environment monitoring and the like is ensured.

11 Claims, 7 Drawing Sheets

US 9,841,376 B2

HIGH SENSITIVITY METAMATERIAL NANO-SENSING SYSTEM WITH ULTRA-NARROW LINE WIDTH SPECTRAL RESPONSE

TECHNICAL FIELD OF THE INVENTION

The invention relates to a metamaterial nano-sensing system, and in particular to a high-sensitivity metamaterial nano-sensing system with an ultra-narrow line width spectral response.

BACKGROUND OF THE INVENTION

A nano-sensing system has the characteristics of no requirement on fluorescent or radioactive isotope labelling, high real-time performance, high automation degree, compact structure, convenience in combination with another technology and the like, and has important and broad application prospect in the fields of biosensing, drug development and detection, environment monitoring and the like.

At present, the most common means for implementing a nanosensor is localized surface plasmon resonance, and a sensor based on such an effect has been commercialized. There are mainly two technical approaches for implementing localized surface plasmon resonance: a metal nanoparticle structure and a periodic metal nanostructure. However, the metal nanoparticle structure is weaker in optical response and poor in repeatability, and a disordered nano-structure group may cause interference to optical response. Even worse, a spectral width is usually hundreds of nanometers, so that the metal nanoparticle structure is low in sensitivity and unfavourable for high-accuracy sensing application. An optical signal of the periodic metal nanostructure is obviously enhanced and easily regenerated, while its spectral width is still unsatisfactory, a corresponding sensor is slightly low in sensitivity, and a practical application of a nanosensor is restricted seriously.

Therefore, in order to further improve sensitivity of the nanosensor, it is urgent to further reduce a line width of its spectral response to make the nanosensor applicable to sensing detection under a severer condition of low-concentration micromolecules and the like by adopting a new means.

SUMMARY OF THE INVENTION

In order to solve the technical problems of large spectral width and low sensitivity of a conventional nanosensor, the invention provides a high-sensitivity metamaterial nano-sensing system with an ultra-narrow line width spectral response, which is compact in structure and convenient to implement.

The technical solution of the invention is as follows: a high-sensitivity metamaterial nano-sensing system with an ultra-narrow line width spectral response is provided, which includes an input light path, a metamaterial nano-sensing unit and an output light unit which are sequentially provided along a direction of a light path, and is characterized in that the metamaterial nano-sensing unit includes a Bragg grating and a metallic periodic array arranged above the Bragg grating, wherein structural parameters of the metallic periodic array and the Bragg grating may be reasonably regulated to implement perfect matching between characteristic impedance and vacuum impedance of the metamaterial nano-sensing unit.

The Bragg grating is formed by dielectric layers which are made from two different materials and sequentially and alternately arranged; and when a wavelength consistent with an impedance perfect matching condition is right located within a forbidden band of the Bragg grating, a perfect absorption phenomenon may occur in the forbidden band, that is, both reflectivity and transmittance of a corresponding position are 0, while absorptivity is 1.

The metallic periodic array is a sub-wavelength metallic periodic array, and a structure size of the metallic periodic array is equivalent to or smaller than a working wavelength.

The metallic periodic array is of a grating structure, a cylinder array structure or a cube array structure; and the metamaterial nano-sensing unit adopting any one of the three metallic periodic array structures may have a wider dynamic sensing range, so that high sensitivity and normal use may still be ensured when refractivity of a sample greatly changes.

A metal in the metallic periodic array is a metallic material, such as gold or silver, capable of exciting a surface plasmon and a Tamm excimer; and a light source may be incident to excite and couple the surface plasmon and the Tamm excimer on a surface of the metal and an interface of the metal and the Bragg grating respectively, thereby generating an ultra-narrow line width spectral response.

There may be one or more metallic periodic arrays, and when there are multiple metallic periodic arrays, different samples to be tested may be injected into different micro-fluidic channels and contact with the surfaces of the corresponding metallic arrays in the metamaterial nano-sensing unit respectively, and refractivity of the multiple different samples is simultaneously tested.

The invention has beneficial effects as follows:
(1) the nano-sensing system has the ultra-narrow line width spectral response, so that sensitivity of a nanosensor is effectively improved, and broad application prospect in the fields of portable biosensing, drug development and detection, environment monitoring and the like is ensured;
(2) the nano-sensing system has the wider dynamic sensing range so as to be applicable to sensing detection an environment where refractivity greatly changes;
(3) the nano-sensing system has the advantages of compact structure, high stability, easiness for integration and convenience in combination with another technology; and
(4) the nano-sensing system may be prepared by virtue of a mature micro-nano machining technology such as electron beam exposure, two-beam laser interference, focused ion beam etching and nano-imprinting, so that low cost and easiness for manufacturing are achieved.

Wherein, drawing reference signs are: 1—light source; 2—incident light; 3—collimation equipment; 4—photoelectric detection equipment; 5—emergent light; 6—display equipment; 7—sample; 8—metallic periodic array; 9—Bragg grating; 10—substrate; 11—metamaterial nano-sensing unit; 12—input light path; 13—output light path; 14—grating; 15—cylinder array; and 16—cube array.

DETAILED DESCRIPTION OF THE EMBODIMENTS

Figure 1:
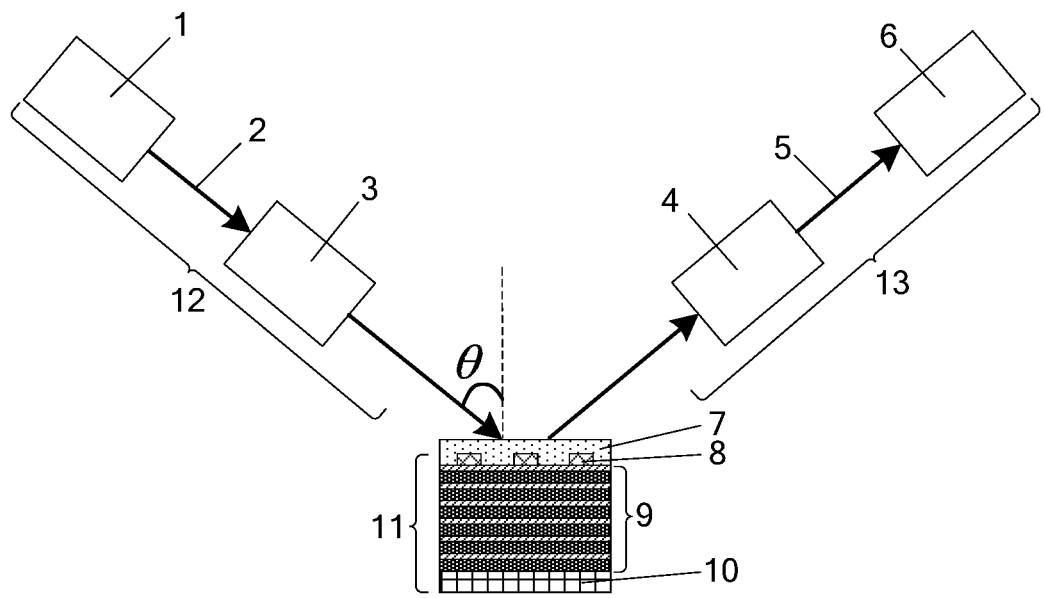
FIG. 1 is a structure diagram of a preferred embodiment of a metamaterial nano-sensing system according to the invention.

As shown in FIG. 1, a structure of a preferred embodiment of a high-sensitivity metamaterial nano-sensing system with an ultra-narrow line width spectral response provided by an invention includes an input light path 12, an output light path 13 and a metamaterial nano-sensing unit 11, wherein the metamaterial nano-sensing unit 11 includes a substrate 10, an Bragg grating 9 and an metallic periodic array 8 which are sequentially provided from bottom to top. The Bragg grating 9 is formed by dielectric layers which are made from two different materials and overlapped. The metallic periodic array 8 is a sub-wavelength metallic periodic array formed by a material, such as gold or silver, capable of exciting a surface plasmon and a Tamm excimer. A structure size of the metallic periodic array 8 is equivalent to or smaller than a working wavelength. The input light path 12 includes a light source 1 and a collimation equipment 3, and the collimation equipment 3 is located between the light source 1 and the metamaterial nano-sensing unit 11; and the output light path 13 includes a photoelectric detection equipment 4 and a display equipment 6, and the photoelectric detection equipment 4 is located between the metamaterial nano-sensing unit 11 and the display equipment 6. The incident light source is a continuous laser light source, a swept source, a white light source or another light source capable of exciting the surface plasmon and the Tamm excimer. Incident light 2 may excite the surface plasmon and the Tamm excimer on a surface of the metallic periodic array 8 and an interface of the metallic periodic array 8 and the Bragg grating 9 respectively. The photoelectric detection equipment 4 should be a spectrograph or equipment with a similar spectral analysis function. The display equipment 6 may receive a signal provided by the photoelectric detection equipment, analyze a relative change of a reflection spectrum of a sample and an uncalibrated reflection spectrum, perform calculation processing on data to obtain refractivity of the sample, and display a result through a display screen.

The Bragg grating 9 and the metallic periodic array 8 above it are sequentially prepared on the substrate 10 through an electron beam evaporation coater, magnetron sputtering equipment or other coating equipment, a periodic structure is manufactured on a metallic thin film by virtue of an electron beam exposure technology, a two-beam laser interference technology, a focused ion beam etching technology, a nano-imprinting technology or another micro-nano machining technology, and a sample to be tested 7 is arranged on a surface of the metallic periodic array 8 through a microfluidic chamber. The metamaterial nano-sensing unit should be calibrated usually before being used, and a calibration process is implemented by placing a sample with known refractivity on the surface of the metallic periodic array 8, then regulating an incident angle θ to maximally narrow a line width of a reflection spectrum, simultaneously testing the reflection spectrum of the sample, recording a result and comparing the reflection spectrum of the sample to be tested and a calibration spectrum to obtain refractivity information of the sample to be tested.

A working principle and specific device parameters of the invention are described as follows.

Figure 2:
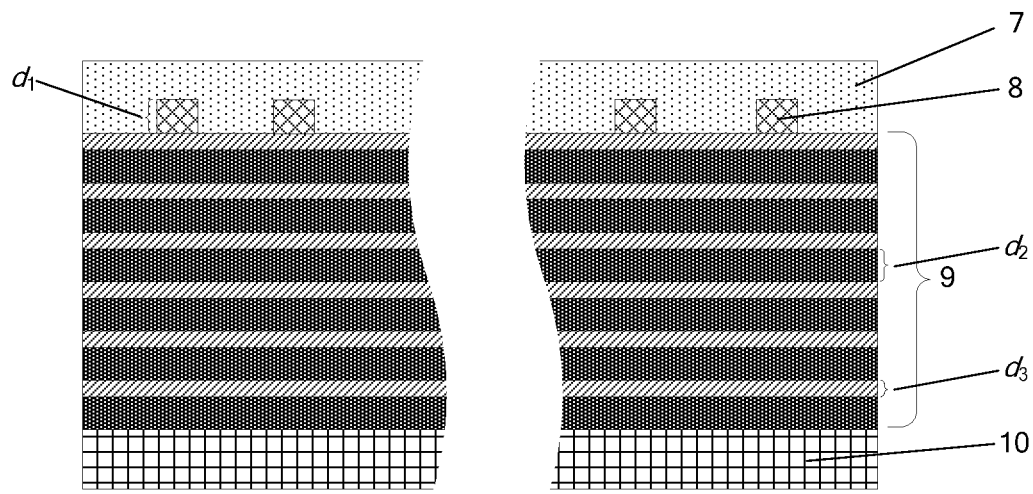
FIG. 2 is a structure diagram of a metamaterial nano-sensing unit with a metallic periodic array.
Figure 3:
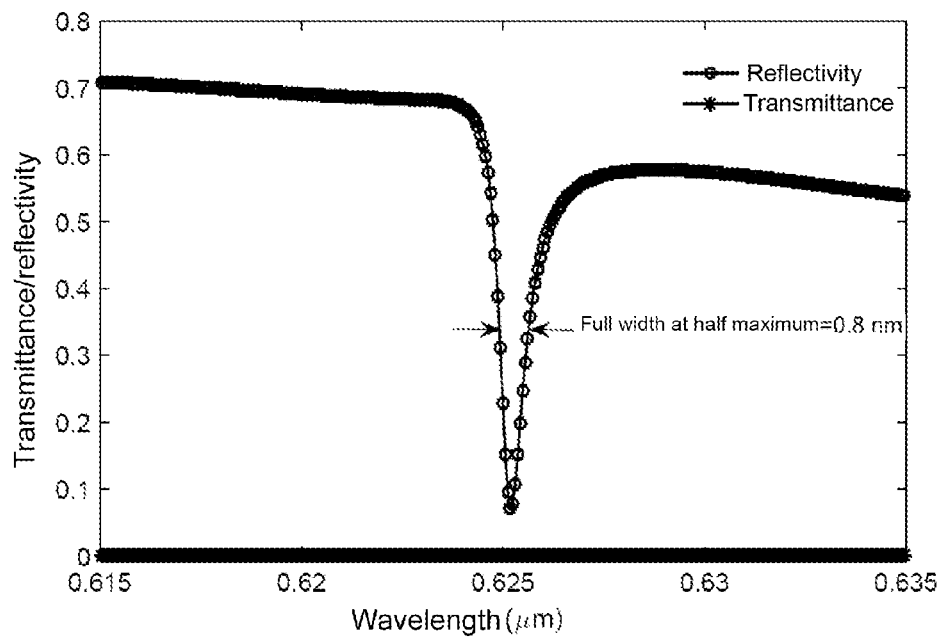
FIG. 3 is a transmission-reflection spectrum of a metamaterial nano-sensing unit according to the invention.

A structure of the metamaterial nano-sensing unit shown in FIG. 2 may be described by virtue of an equivalent transmission line model, the metallic periodic array 8 and the two kinds of dielectric layers in the Bragg grating 9 may be considered as equivalent impedance according to the model, characteristic impedance values are represented by $Z_m$, $Z_a$ and $Z_b$ respectively, and characteristic impedance of the metamaterial nano-sensing unit may be represented as a function of the three equivalent impedance: $Z_{sen}=f(Z_m, Z_a, Z_b)$. Structural parameters of the metallic periodic array 8 and the Bragg grating 9 may be reasonably regulated to implement perfect matching between the characteristic impedance $Z_{sen}$ and vacuum impedance $Z_0$ of the metamaterial nano-sensing unit, that is, $Z_{sen}=Z_0$, and if a wavelength consistent with an impedance perfect matching condition is right located within a forbidden band of the Bragg grating, a perfect absorption phenomenon may occur in the forbidden band, that is, both reflectivity and transmittance of a corresponding position are 0, while absorptivity is 1. In addition, the incident light may excite the surface plasmon on a surface of the metal and excite the Tamm excimer on an interface of the metal and the Bragg grating, the surface plasmon and the Tamm excimer may be coupled to generate an ultra-narrow line width spectral response, FIG. 3 is a transmission-reflection spectrum of a metamaterial nano-sensing unit, and a full width at half maximum of the reflection spectrum is only 0.8 nm.

Figure 4A:
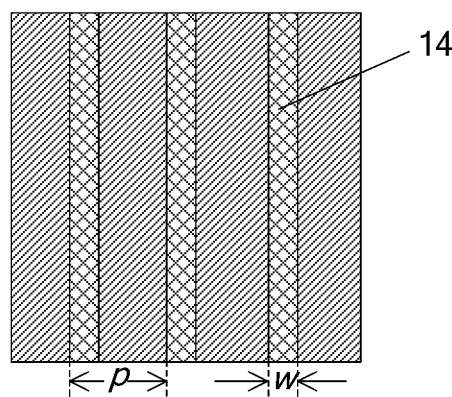
FIG. 4A is a structure diagram of a sub-wavelength metallic periodic array with a grating structure.
Figure 4B:
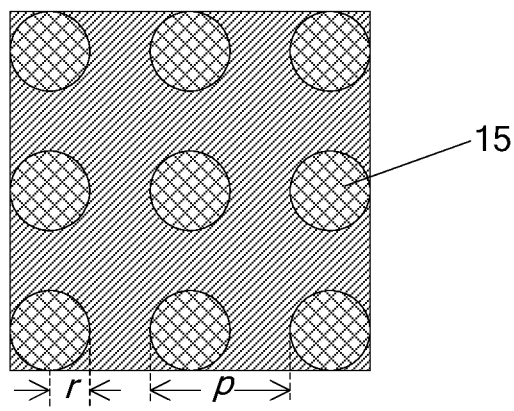
FIG. 4B is a structure diagram of a wave-length metallic periodic array with a cylinder array structure.
Figure 4C:
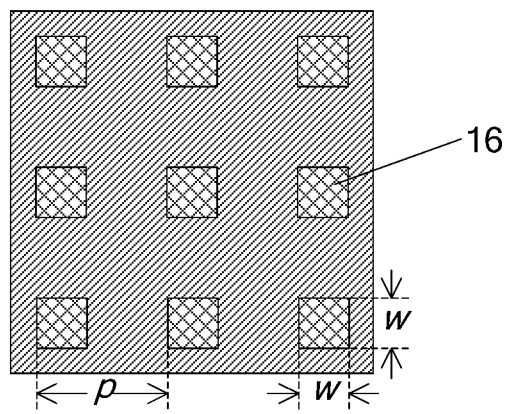
FIG. 4C is a structure diagram of a wave-length metallic periodic array with a cube array structure.

As shown in FIG. 4A-4C, the sub-wavelength metallic periodic array may be formed by three structure forms, i.e. a grating 14, a cylinder array 15 and a cube array 16. The metallic periodic array adopting any one of the three forms may be prepared by virtue of a mature micro-nano machining technology such as electron beam exposure, two-beam laser interference, focused ion beam etching and nano-imprinting.

Figure 5A:
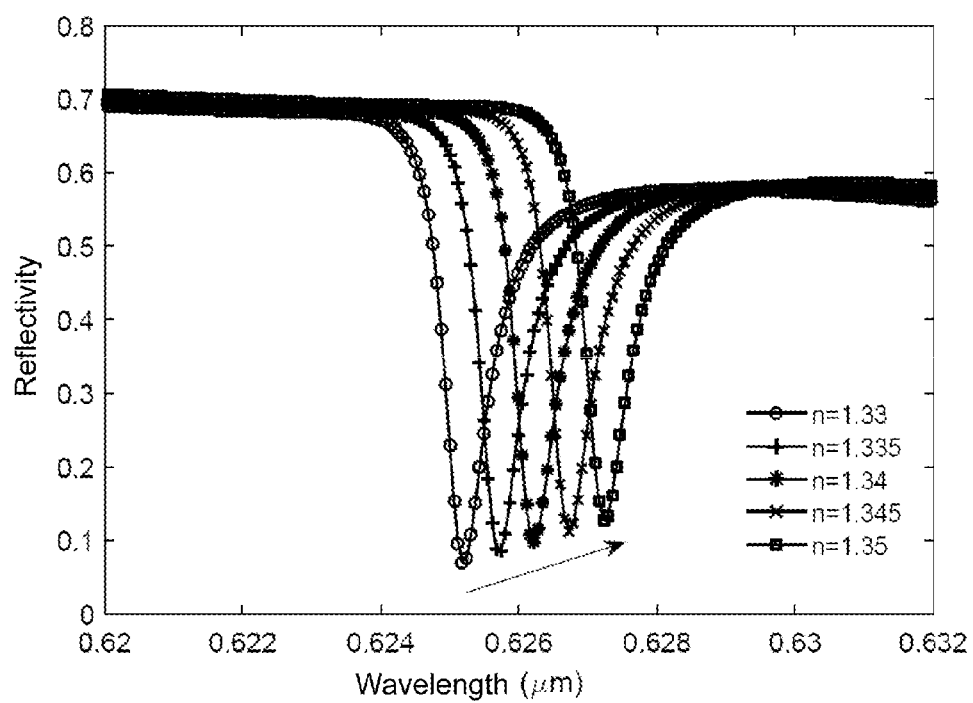
FIG. 5A is a spectral response of a metamaterial nano-sensing system with a grating structure corresponding to refractivity of different samples.
Figure 5B:
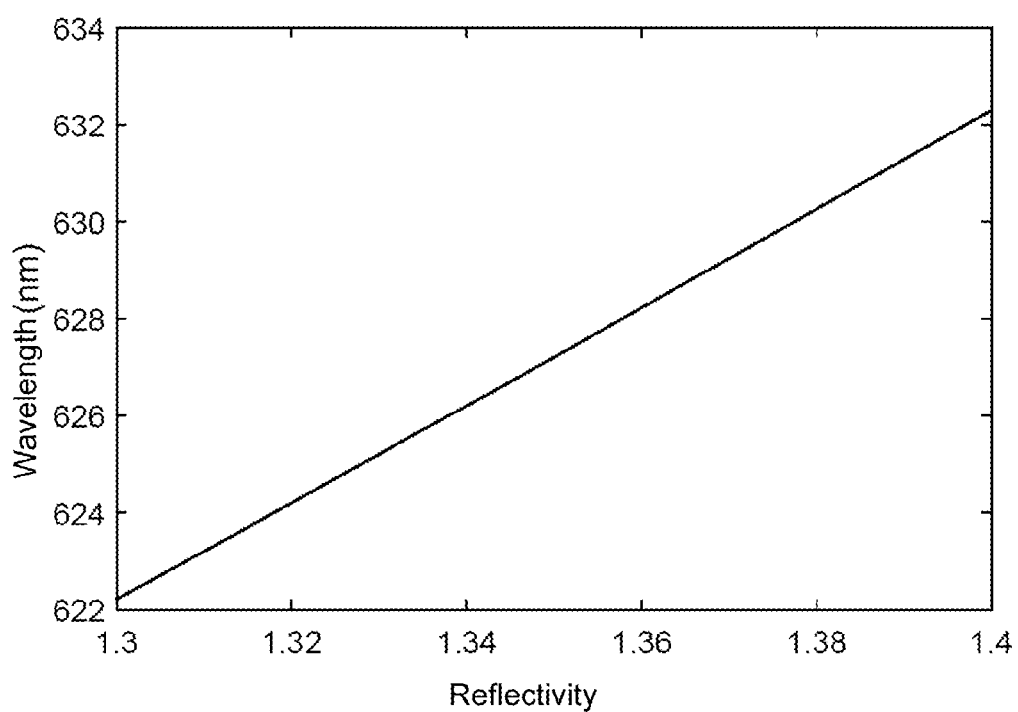
FIG. 5B is a relationship between a wavelength, consistent with an impedance matching condition, of a metamaterial nano-sensing system with a grating structure and refractivity of a sample.
Figure 6A:
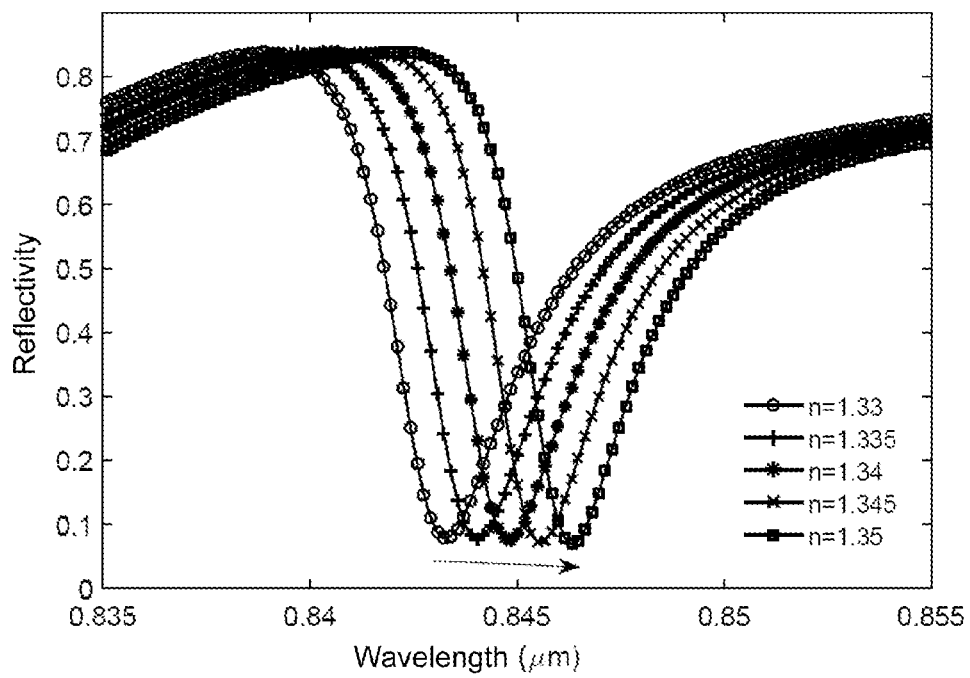
FIG. 6A is a spectral response of a metamaterial nano-sensing system with a cylinder array structure to refractivity of different samples.
Figure 6B:
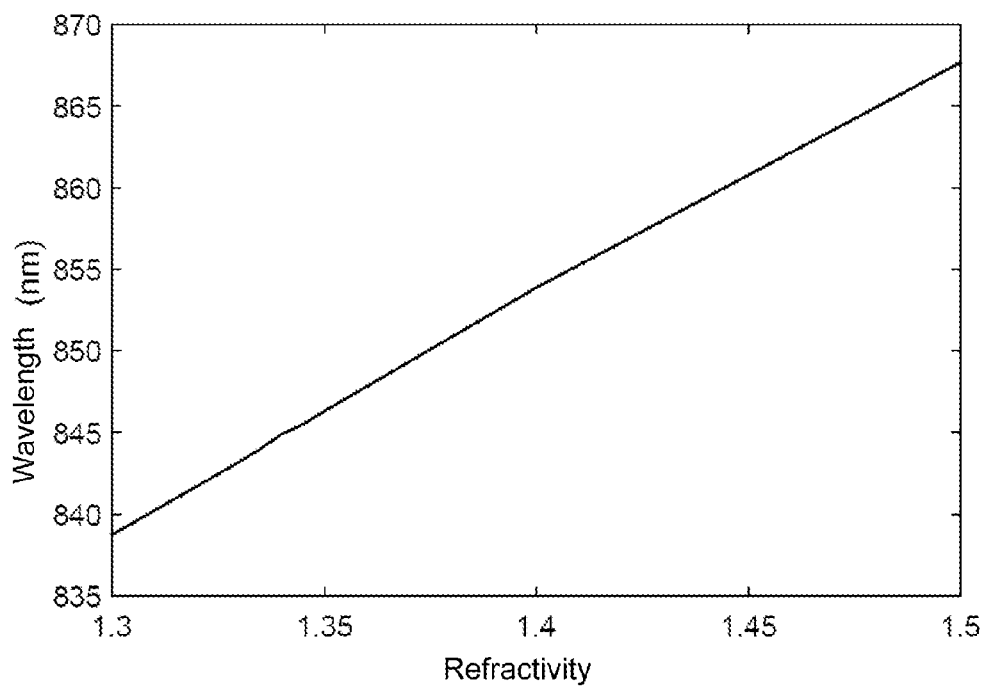
FIG. 6B is a relationship between a wavelength, consistent with an impedance matching condition, of a metamaterial nano-sensing system with a cylinder array structure and refractivity of a sample.
Figure 7A:
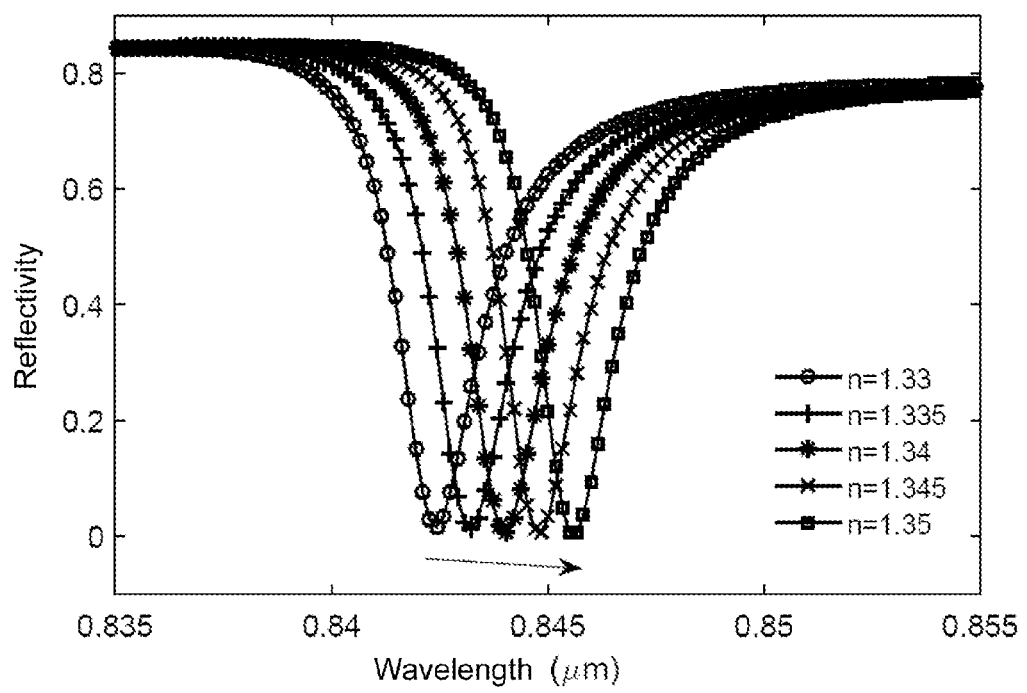
FIG. 7A is a spectral response of a metamaterial nano-sensing system with a cube array structure to refractivity of different samples.
Figure 7B:
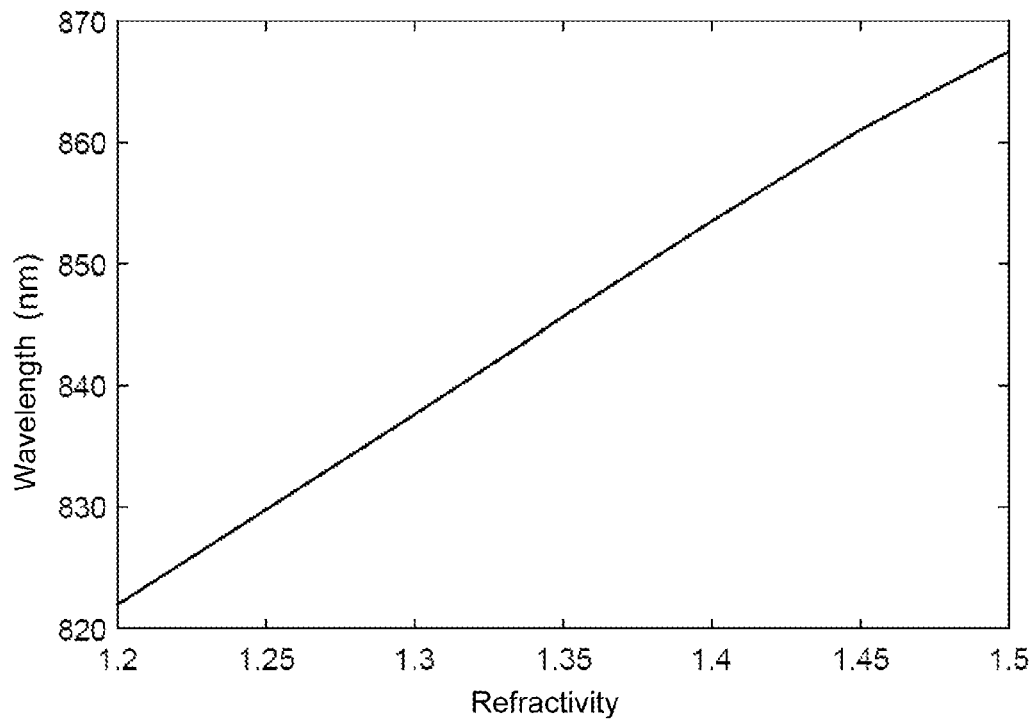
FIG. 7B is a relationship between a wavelength, consistent with an impedance matching condition, of a metamaterial nano-sensing system with a cube array structure and refractivity of a sample.

The structural parameters of the metallic periodic array shown in FIG. 4A-4C are set to be ($d_1$=90 nm, $d_2$=100 nm, $d_3$=85 nm, p=278 nm, w=139 nm), ($d_1$=150 nm, $d_2$=140 nm, $d_3$=80 nm, p=380 nm, r=100 nm) and ($d_1$=150 nm, $d_2$=140 nm, $d_3$=80 nm, p=380 nm, w=200 nm), and when an incident angle of the light source is 30 degrees, if the refractivity of the sample to be tested on the surface of the metallic periodic array changes, effective refractivity of a localized light field on the surface of the metallic periodic array may be changed to make the wavelength consistent with the impedance perfect matching condition (i.e. a wavelength corresponding to minimum reflectivity in the reflection spectrum) drift, and drift of the wavelength corresponding to the minimum reflectivity in the reflection spectrum may be measured to obtain a change in the refractivity of the sample on the surface of the metallic periodic array. Results of reflection spectrum line and refractivity change rules corresponding to metamaterial nano-sensing units with the three different structures are shown in FIG. 5 to FIG. 7, wherein the two dielectric materials forming the Bragg grating are, for example, $SiO_2$ and $TiO_2$ respectively, and the substrate is a dielectric material with refractivity of 1.5. Since the reflection spectrum of the metamaterial nano-sensing unit has an ultra-narrow line width, a Figure of Merit (FOM) capable of reaching 125 and higher sensitivity, the problems of large spectral width and low sensitivity of a conventional nanosensor are solved. In addition, the metamaterial nano-sensing unit adopting any one of the three structure forms has a wider dynamic sensing range, so that high sensitivity and normal use may still be ensured when the refractivity of the sample greatly changes.

In order to reduce influence of noise (such as light source noise, sample temperature noise and detector noise) on a result in a sensing test, the incident angle of the light source may be changed, the working wavelength of the nanosensor may be regulated, changes in refractivity of the sample under different incident angles may be tested, and results may be statistically averaged.

Figure 8:
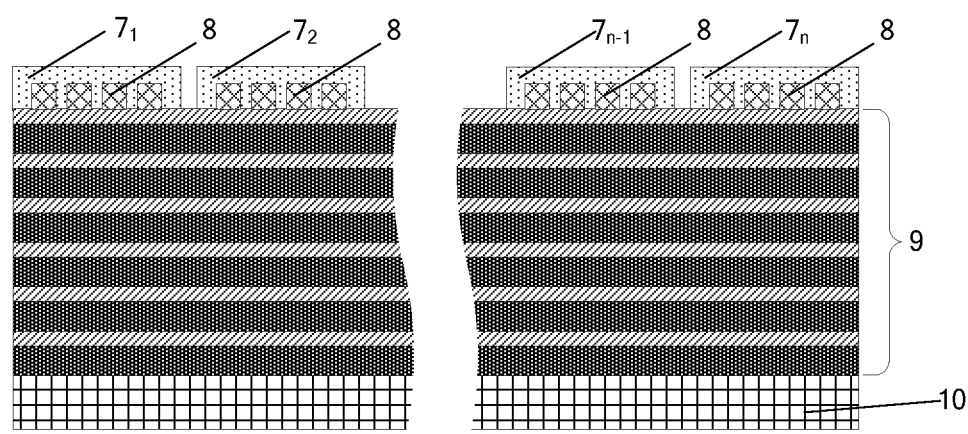
FIG. 8 is a structure diagram of a metamaterial nano-sensing unit with multiple metallic periodic arrays.

In order to simultaneously test refractivity of multiple samples, multiple metallic periodic arrays may be combined for use in the same metamaterial nano-sensing unit, as shown in FIG. 8. By a current mature microfluidic technology, different samples to be tested $7_1$-$7_n$ are injected into different microfluidic channels and contact with surfaces of the corresponding metallic arrays in the metamaterial nano-sensing unit respectively, the incident light may be generated by one or more light sources, and at the same time, the incident light is incident to the surface of the metamaterial nano-sensing unit, and is reflected, a spectrum of each reflected beam is received and analyzed by the photoelectric detection equipment, results are transmitted to the display equipment, and refractivity numerical values of each sample are calculated by the display equipment.

Since the metamaterial nano-sensing system provided by the invention has the ultra-narrow line width spectral response, the problems of excessive spectral width and lower sensitivity of the conventional nanosensor are solved. By the nanosensor, the ultra-narrow line width spectral response and higher sensitivity are achieved; and the multiple metallic periodic arrays may be combined to realize a function of simultaneously testing refractivity of multiple samples, so that important application value in the fields of portable biosensing, drug detection, environment monitoring and the like is ensured.

The invention claimed is:

1. A high-sensitivity metamaterial nano-sensing system with an ultra-narrow line width spectral response, comprising an input light path, metamaterial nano-sensing unit and output light path which are sequentially provided along a direction of a light path, wherein the metamaterial nano-sensing unit comprises a Bragg grating and a metallic periodic array arranged above the Bragg grating, wherein the Bragg grating is formed by dielectric layers which are made from two different materials and arranged sequentially and alternately.

2. The high-sensitivity metamaterial nano-sensing system with the ultra-narrow line width spectral response according to claim 1, wherein the metallic periodic array is a sub-wavelength metallic periodic array.

3. The high-sensitivity metamaterial nano-sensing system with the ultra-narrow line width spectral response according to claim 2, wherein the metallic periodic array is of a grating structure, a cylinder array structure or a cube array structure.

4. The high-sensitivity metamaterial nano-sensing system with the ultra-narrow line width spectral response according to claim 3, wherein a metal in the metallic periodic array is a metallic material capable of exciting a surface plasmon and a Tamm excimer.

5. The high-sensitivity metamaterial nano-sensing system with the ultra-narrow line width spectral response according to claim 1, wherein there is one or more metallic periodic arrays.

6. The high-sensitivity metamaterial nano-sensing system with the ultra-narrow line width spectral response according to claim 5, wherein the input light path comprises a light source and a collimation equipment, and the collimation equipment is located between the light source and the metamaterial nano-sensing unit; and the output light path comprises a photoelectric detection equipment and a display equipment, and the photoelectric detection equipment is located between the metamaterial nano-sensing unit and the display equipment.

7. The high-sensitivity metamaterial nano-sensing system with the ultra-narrow line width spectral response according to claim 6, wherein the light source is a continuous laser light source, a swept source, a white light source or another light source capable of exciting the surface plasmon and the Tamm excimer; and the photoelectric detection equipment is a spectrograph or other equipment with a spectral analysis function.

8. The high-sensitivity metamaterial nano-sensing system with the ultra-narrow line width spectral response according to claim 7, wherein a substrate is arranged below the Bragg grating.

9. The high-sensitivity metamaterial nano-sensing system with the ultra-narrow line width spectral response according to claim 2, wherein there is one or more metallic periodic arrays.

10. The high-sensitivity metamaterial nano-sensing system with the ultra-narrow line width spectral response according to claim 3, wherein there is one or more metallic periodic arrays.

11. The high-sensitivity metamaterial nano-sensing system with the ultra-narrow line width spectral response according to claim 4, wherein there is one or more metallic periodic arrays.

* * * * *